US011452887B2

(12) United States Patent
Kim et al.

(10) Patent No.: US 11,452,887 B2
(45) Date of Patent: Sep. 27, 2022

(54) ULTRASONIC STIMULATION DEVICE USING GUIDE FRAMEWORK

(71) Applicant: KOREA INSTITUTE OF SCIENCE AND TECHNOLOGY, Seoul (KR)

(72) Inventors: Hyung Min Kim, Seoul (KR); Inchan Youn, Seoul (KR); Seung-Jong Kim, Seoul (KR); Junhyuk Choi, Seoul (KR); Hongchae Baek, Seoul (KR); Chan Yul Jung, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 613 days.

(21) Appl. No.: 15/695,804

(22) Filed: Sep. 5, 2017

(65) Prior Publication Data
US 2018/0064960 A1    Mar. 8, 2018

(30) Foreign Application Priority Data
Sep. 5, 2016 (KR) .......................... 10-2016-0113949

(51) Int. Cl.
*A61N 7/00* (2006.01)
*A61B 90/10* (2016.01)
(Continued)

(52) U.S. Cl.
CPC ................ *A61N 7/00* (2013.01); *A61B 90/10* (2016.02); *A61B 90/11* (2016.02); *A61B 90/18* (2016.02);
(Continued)

(58) Field of Classification Search
CPC ... A61B 2090/502; A61B 90/10; A61B 90/11; A61B 90/18; A61N 2007/0026;
(Continued)

(56) References Cited

U.S. PATENT DOCUMENTS 8,603,014 B2   12/2013   Alleman et al.
8,613,714 B2   12/2013   Alleman et al.
(Continued)

FOREIGN PATENT DOCUMENTS

JP         4992034 B2      8/2012
KR    10-0974531 B1        8/2010
(Continued)

*Primary Examiner* — Yi-Shan Yang
*Assistant Examiner* — Alexei Bykhovski
(74) *Attorney, Agent, or Firm* — Insight Law Group, PLLC; Seung Lee

(57) ABSTRACT

A guide framework for positioning an ultrasonic transducer which emits a focused ultrasound to a target point in carrying out surgery to apply ultrasonic stimulation to a subject's brain, includes a body in a shape of a mask that is laid on the subject's face, and a positioning hole formed through an inner surface and an outer surface of the mask body, the positioning hole into which the ultrasonic transducer is inserted, wherein the inner surface of the mask body is formed to conform a facial contour of the subject, and when the guide framework is laid on the subject's face and the ultrasonic transducer is disposed at the positioning hole, the position of the target point is naturally disposed at a preset stimulation site of the brain. An ultrasonic stimulation device includes an ultrasonic transducer and the guide framework for positioning the ultrasonic transducer.

17 Claims, 16 Drawing Sheets

(51) Int. Cl.
*A61B 90/18* (2016.01)
*A61B 90/11* (2016.01)
*A61B 90/50* (2016.01)

(52) U.S. Cl.
CPC ... *A61B 2090/502* (2016.02); *A61N 2007/006* (2013.01); *A61N 2007/0026* (2013.01); *A61N 2007/0078* (2013.01); *A61N 2007/0082* (2013.01)

(58) Field of Classification Search
CPC ...... A61N 2007/006; A61N 2007/0078; A61N 2007/0082; A61N 7/00
See application file for complete search history.

(56) References Cited

U.S. PATENT DOCUMENTS

| | | |
|---|---|---|
| 8,956,277 B2 | 2/2015 | Mishelevich |
| 9,020,612 B1 | 4/2015 | Danilov et al. |
| 9,393,401 B2 | 7/2016 | Goldwasser et al. |
| 10,149,618 B1* | 12/2018 | Tandon ............... A61B 5/0042 |
| 2003/0131852 A1* | 7/2003 | Shafer .................. A61B 90/14 |
| | | 128/206.21 |
| 2011/0251489 A1* | 10/2011 | Zhang ................. A61B 8/4227 |
| | | 600/459 |
| 2012/0289869 A1 | 11/2012 | Tyler |
| 2013/0281890 A1* | 10/2013 | Mishelevich ...... A61N 1/36107 |
| | | 601/2 |
| 2014/0155747 A1* | 6/2014 | Bennett .................... A61N 7/02 |
| | | 600/439 |
| 2014/0188011 A1 | 7/2014 | Wurster et al. |
| 2015/0025414 A1* | 1/2015 | Rhad ...................... A61B 90/17 |
| | | 600/567 |
| 2016/0166234 A1* | 6/2016 | Zhang .................. A61B 8/4416 |
| | | 600/427 |
| 2016/0185056 A1* | 6/2016 | Beacham ........... B29D 11/0099 |
| | | 264/2.7 |
| 2016/0243381 A1 | 8/2016 | Alford et al. |
| 2017/0065835 A1 | 3/2017 | Park |
| 2017/0171677 A1* | 6/2017 | Norris .................... H04R 25/75 |
| 2017/0209717 A1* | 7/2017 | Bonutti ..................... A61N 7/00 |
| 2017/0224978 A1 | 8/2017 | Lee |

FOREIGN PATENT DOCUMENTS

| | | |
|---|---|---|
| KR | 10-1418356 B1 | 7/2014 |
| KR | 10-2015-0055613 A | 5/2015 |
| KR | 10-1525450 B1 | 6/2015 |
| KR | 10-2015-0106744 A | 9/2015 |
| WO | WO 2013/184993 A1 | 12/2013 |
| WO | WO 2015/130124 A1 | 9/2015 |
| WO | WO 2016/135475 A1 | 9/2016 |

* cited by examiner

ULTRASONIC STIMULATION DEVICE USING GUIDE FRAMEWORK

CROSS-REFERENCE TO RELATED APPLICATION

This application claims priority to Korean Patent Application No. 10-2016-0113949, filed on Sep. 5, 2016, and all the benefits accruing therefrom under 35 U.S.C. § 119, the contents of which in its entirety are herein incorporated by reference.

BACKGROUND

1. Field

The present disclosure relates to an ultrasonic stimulation device, and more particularly, to a guide framework for positioning an ultrasonic transducer in carrying out surgery to apply ultrasonic stimulation to the brain of a subject, and an ultrasonic stimulation device using the same.

DESCRIPTION ABOUT NATIONAL RESEARCH AND DEVELOPMENT SUPPORT

This study was supported by the Brain Science Source Technology Development Project of Ministry of Science, ICT and Future Planning, Republic of Korea (Development of MRI-based image-guided brain stimulation control system for internet game addiction treatment, Project No. 1711029671) under the Korea Institute of Science and Technology.

2. Description of the Related Art

To treat brain diseases or investigate the brain activity, studies or treatments are done based on delivery of stimulation to the brain and observation or induction of its responses.

A typical neural stimulation method is electrical stimulation, but the limitations of the electrical stimulation method are that a process for inserting electrodes is necessary and involves invasion into a patient's body, and targeted stimulation to a specific site is difficult due to a chain of electrical reactions in the living body.

To overcome these limitations, studies are made on a method that produces focused ultrasound using an ultrasonic transducer, targets the focus position of the focused ultrasound to a desired stimulation location, and delivers stimulation.

FIG. 1 is a schematic diagram of an ultrasonic transducer 200 for producing ultrasonic waves.

As shown in FIG. 1, the ultrasonic transducer 200 includes a body 211 that is open to one side, and a piezoelectric element 213 formed at the opening of the body 211. An inside 212 of the body 211 is filled with air. An electric wire is connected to the piezoelectric element 213 to apply voltage to the piezoelectric element 213.

The piezoelectric element 213 exploits a material that exhibits the piezoelectric effect, such as quartz and turmaline, and the ultrasonic transducer 200 produces and outputs ultrasonic waves using the piezoelectric effect of the piezoelectric element 213.

FIGS. 2A to 2C are diagrams illustrating the piezoelectric effect of the piezoelectric element 213.

As shown in FIGS. 2A to 2C, when tension and compression is repeatedly applied along one axis of the piezoelectric element 213 made of quartz crystals, positive charge (+) is created on one side and negative charge (−) is created on the other side, producing an electric current.

This polarization phenomenon of the piezoelectric element 213 occurs due to a change in relative position of (+) ions and (−) ions as the crystal structure distorts. Thus, the center of gravity of charges having moved the position in the element is automatically corrected, but an electric field is formed across the crystal. The electric field is in opposite directions under compression and tension.

On the contrary, when voltage is applied across the piezoelectric element 213, (+) ions in the electric field move to (−) electrode, and (−) ions move to (+) electrode. By the inverse piezoelectric effect, tension and compression is induced in the piezoelectric element 213 based on the direction of voltage applied from the outside.

As the piezoelectric element 213 is repeatedly subjected to tension and compression, ultrasonic waves with frequencies higher than the audible range are produced in the similar principle to the operation principle of a speaker. In this instance, when the piezoelectric element 213 is formed in a concave shape, focused ultrasound focusing at one focal point may be formed.

To target the focus position of focused ultrasound to a desired target location using the ultrasonic transducer 200 with the unsteerable focus position and the fixed focal length from the ultrasonic transducer 200, it is necessary to move the position of the ultrasonic transducer 200 itself.

As shown in FIG. 3, according to the related art, to place the position of a focal point 215 of ultrasound 214 of the ultrasonic transducer 200 at a target location O, it is possible to move the position of the ultrasonic transducer 200 with regard to 3-axis using motors 51, 52, 53.

According to this configuration, the position control of the ultrasonic transducer 200 will be performed by controlling the rotational angle of each motor 51, 52, 53 to direct a central position O' of the ultrasonic transducer 200 to a specific location.

As the ultrasonic transducer 200 has the fixed focal length, it is relatively accurate and simple to calculate the central position O' of the ultrasonic transducer 200 for having the desired focus position O through the corresponding focus position. However, a control error may occur in the course of controlling each motor 51, 52, 53 to control the central position O' of the ultrasonic transducer 200.

Meanwhile, to identify a stimulation effect of ultrasonic waves produced by the ultrasonic transducer 200, studies are made on monitoring in real time through magnetic resonance imaging after ultrasonic stimulation is performed in magnetic resonance imaging (MRI) machine.

As shown in FIGS. 4 and 5, a typical MRI machine 2 has a structure in which a patient 1 lies on a bed 20, which then moves into a narrow space 30, and the body of the patient 1 is imaged. Particularly, for imaging of the brain, a head support 21 is installed to allow the patient 1 to make less head movements, and a cage 22 is installed above the face.

Accordingly, to apply ultrasonic stimulation using the ultrasonic transducer 200 in the MRI machine 2, the ultrasonic transducer 200 should be installed in a very narrow space.

A positioning tool of the ultrasonic transducer 200 according to the related art as described in FIG. 3 has too large spatial limitation to install it in the MRI machine 2 because its volume is large due to motors.

Moreover, apart from the known MRI-compatible ultrasonic transducer 200, various types of electric devices including motors should be designed as MRI-compatible devices, which significantly increases the manufacturing costs.

SUMMARY

The present disclosure is designed to solve the problems of the related art, and therefore, the present disclosure is directed to providing a guide framework for positioning an ultrasonic transducer without an electric control device, and an ultrasonic stimulation device for placing the focus position of the ultrasonic transducer at a desired location through the corresponding guide framework.

To achieve the object, according to an aspect of the present disclosure, there is provided a guide framework for positioning an ultrasonic transducer which emits a focused ultrasound to a target point in carrying out surgery to apply ultrasonic stimulation to a subject's brain, the guide framework including a body in a shape of a mask that is laid on the subject's face, and a positioning hole formed through an inner surface and an outer surface of the mask body, the positioning hole into which the ultrasonic transducer is inserted, wherein the inner surface of the mask body is formed to conform a facial contour of the subject, and when the guide framework is laid on the subject's face and the ultrasonic transducer is disposed at the positioning hole, the position of the target point is naturally disposed at a preset stimulation site of the brain.

According to an embodiment, the mask body may be formed to cover an upper part of the subject's face with the subject's nose uncovered.

According to an embodiment, the positioning hole may be formed of a slit that is cut open to one side of the mask body, and when the ultrasonic transducer is disposed at an edge on an opposite side of an opening of the slit, the position of the target point may be naturally disposed at a preset stimulation site of the brain.

According to an embodiment, the guide framework may be formed by a 3-dimensional printing process.

According to an embodiment, the guide framework may further include an acoustic lens which is inserted into the positioning hole and disposed between the ultrasonic transducer and the subject's face to correct the position of the target point to which the ultrasound is focused.

According to an embodiment, the acoustic lens may be formed by a 3-dimensional printing process.

According to an embodiment, the acoustic lens may be tailored to focus the ultrasound to at least two target points separately.

According to an embodiment, the guide framework may further include additional positioning holes into which additional ultrasonic transducers for focusing the ultrasound to target points different from the target point are inserted.

According to another aspect of the present disclosure, there is provided an ultrasonic stimulation device for carrying out surgery to apply ultrasonic stimulation to a subject's brain, the ultrasonic stimulation device including an ultrasonic transducer configured to emit a focused ultrasound focused to a target point, and the guide framework for positioning the ultrasonic transducer.

According to an embodiment, the ultrasonic stimulation device may further include a fixing device for fixing the ultrasonic transducer, wherein the fixing device adjusts the position of the ultrasonic transducer in 3 dimensions to dispose the ultrasonic transducer at the positioning hole.

According to an embodiment, the fixing device may have a shape of a headphone that is supported and fixed on a side of the subject's face.

According to an embodiment, the fixing device may include two earmuffs which cover two ears of the subject, and an arch-shaped connecting member connecting the two earmuffs, and the ultrasonic transducer may be connected to the connecting member.

According to an embodiment, the connecting member may be rotatable frontward and rearward of the subject with respect to the earmuffs, the position of the ultrasonic transducer may be moveable laterally along a lengthwise direction of the connecting member, and the position of the ultrasonic transducer may be moveable in a radius direction apart from or close to the connecting member.

According to an embodiment, the positioning hole may be formed in a shape of a slit that is cut open to one side of the mask body, and when the ultrasonic transducer is fixedly positioned at an edge on an opposite side of an opening of the slit, the guide framework may be removable.

A method for manufacturing a guide framework according to still another aspect of the present disclosure includes collecting contour information by scanning a facial contour of the subject, setting 3-dimensional coordinates of a stimulation location, and setting center coordinates of the ultrasonic transducer in consideration of a focal length to place a target point at the corresponding stimulation location, setting a central position of a positioning hole and a protrusion height using shape information of the ultrasonic transducer to position the ultrasonic transducer at the center coordinates, setting a thickness and a size of a mask body, and manufacturing a guide framework by a 3-dimensional printing process based on the contour information, the center coordinates, the central position, the protrusion height, and the thickness and size information of the mask body.

According to an embodiment, there is provided a computer program for performing the method for manufacturing a guide framework.

DETAILED DESCRIPTION

Figure 1:
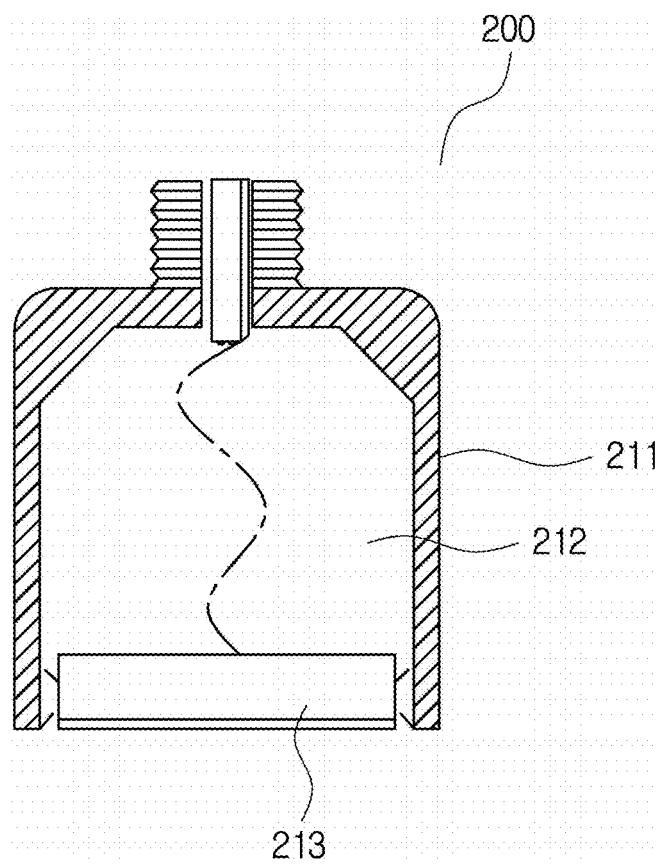
FIG. 1 is a schematic diagram illustrating the structure of an ultrasonic transducer.

Hereinafter, the preferred embodiments of the present disclosure are described with reference to the accompanying drawings. The present disclosure is described by referring to the embodiments shown in the drawings, but this is provided for illustration only, and the technical spirit of the present disclosure and its key elements and operation are not limited thereby.

Figure 6:
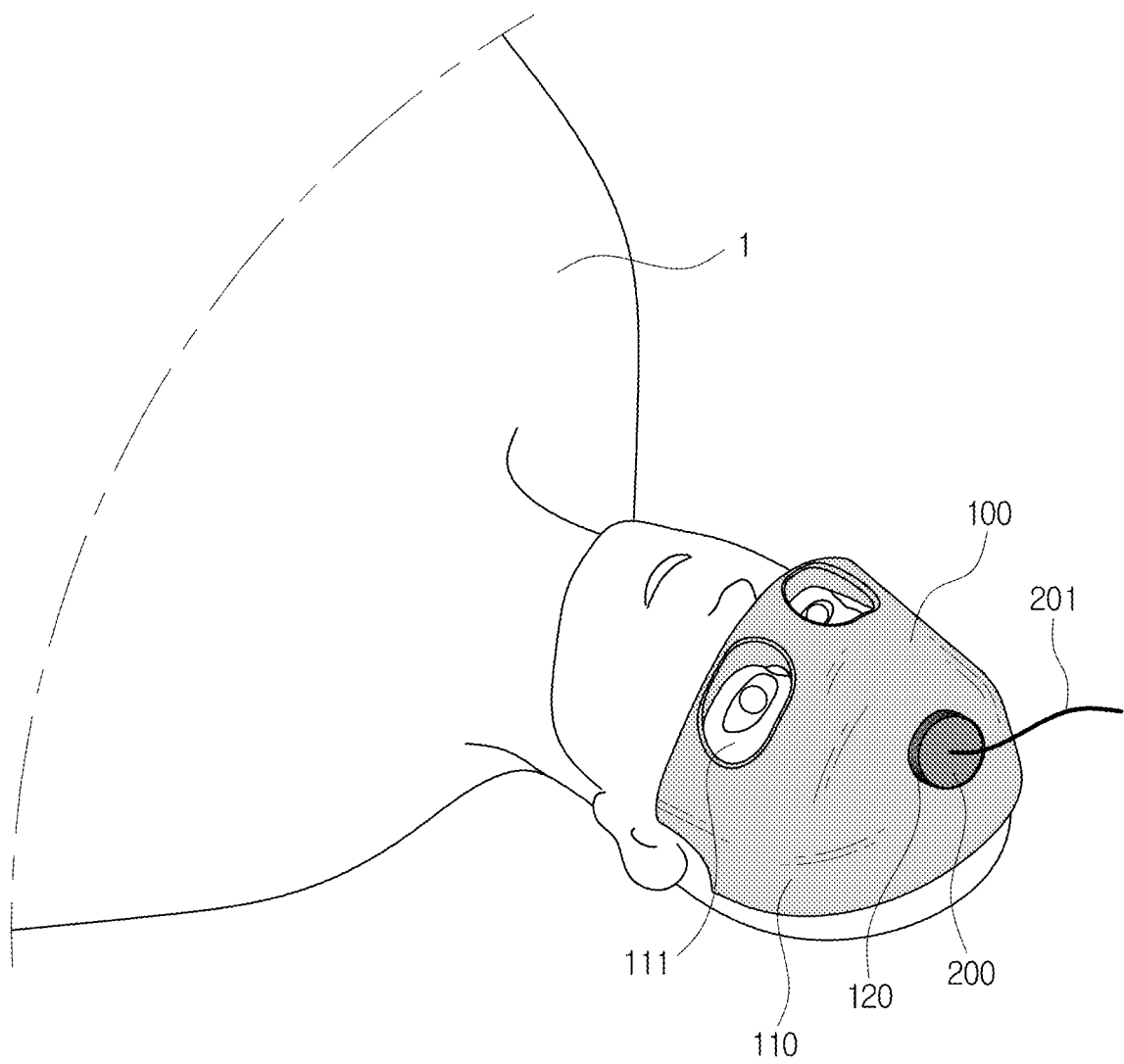
FIG. 6 shows an ultrasonic stimulation device according to an embodiment of the present disclosure.

FIG. 6 shows an ultrasonic stimulation device according to an embodiment of the present disclosure.

The ultrasonic stimulation device according to this embodiment is an ultrasonic stimulation device for carrying out surgery to apply ultrasonic stimulation to the brain of a subject, and includes an ultrasonic transducer 200 to emit a focused ultrasound 214 focused to a focal point (e.g. target point) 215, and a guide framework 100 to position the ultrasonic transducer 200.

Figure 7A:
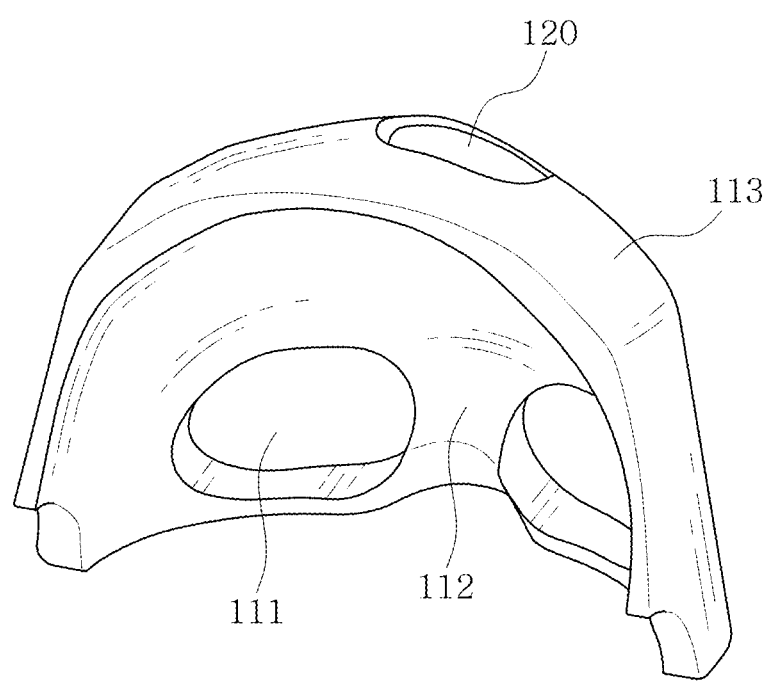
FIG. 7A is a rear perspective view of a guide framework of the ultrasonic stimulation device of FIG. 6.

FIG. 7A is a rear perspective view of the guide framework 100.

Referring to FIGS. 6 and 7A, the guide framework 100 includes a mask body 110 in a shape of a mask that is laid on the face of the subject 1, and a positioning hole 120 formed through an inner surface 112 and an outer surface 113 of the mask body 110, into which the ultrasonic transducer 200 can be inserted.

Figure 7B:
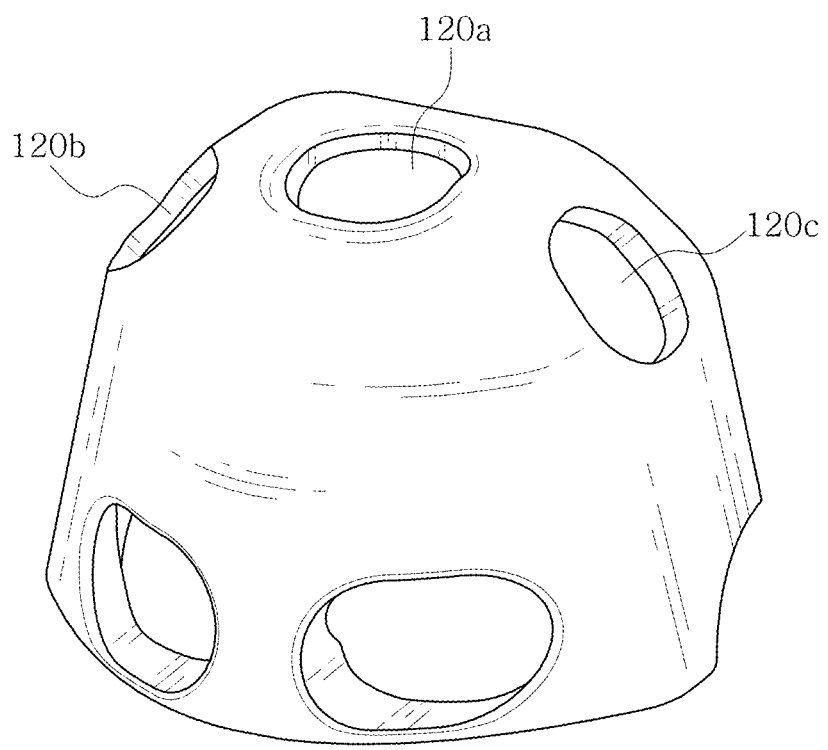
FIG. 7B is a perspective view of a guide framework including additional positioning holes.

FIG. 7B is a perspective view of a guide framework including additional positioning holes.

Referring to FIG. 7B, the guide framework may be further formed to include additional positioning holes 120b and 120c into which additional ultrasonic transducers for focusing ultrasound at different target points may be inserted.

The mask body 110 is formed to cover the upper part of the face of the subject, while not fully covering the nose of the subject 1 to keep the subject from feeling trapped during ultrasonic stimulation surgery. Furthermore, the mask body 110 includes an opening 111 not to cover the eyes of the subject 1.

The positioning hole 120 according to this embodiment is formed of a circular through-hole to match the shape of the ultrasonic transducer 200. According to this embodiment, as the brain of the subject 1 is expected to be stimulated through the ultrasonic transducer 200, the positioning hole 120 is formed to be disposed at the forehead or head of the subject 1.

The ultrasonic transducer 200 may be inserted into and fixed to the positioning hole 120, and the position is determined by the guide framework 100.

Figure 8:
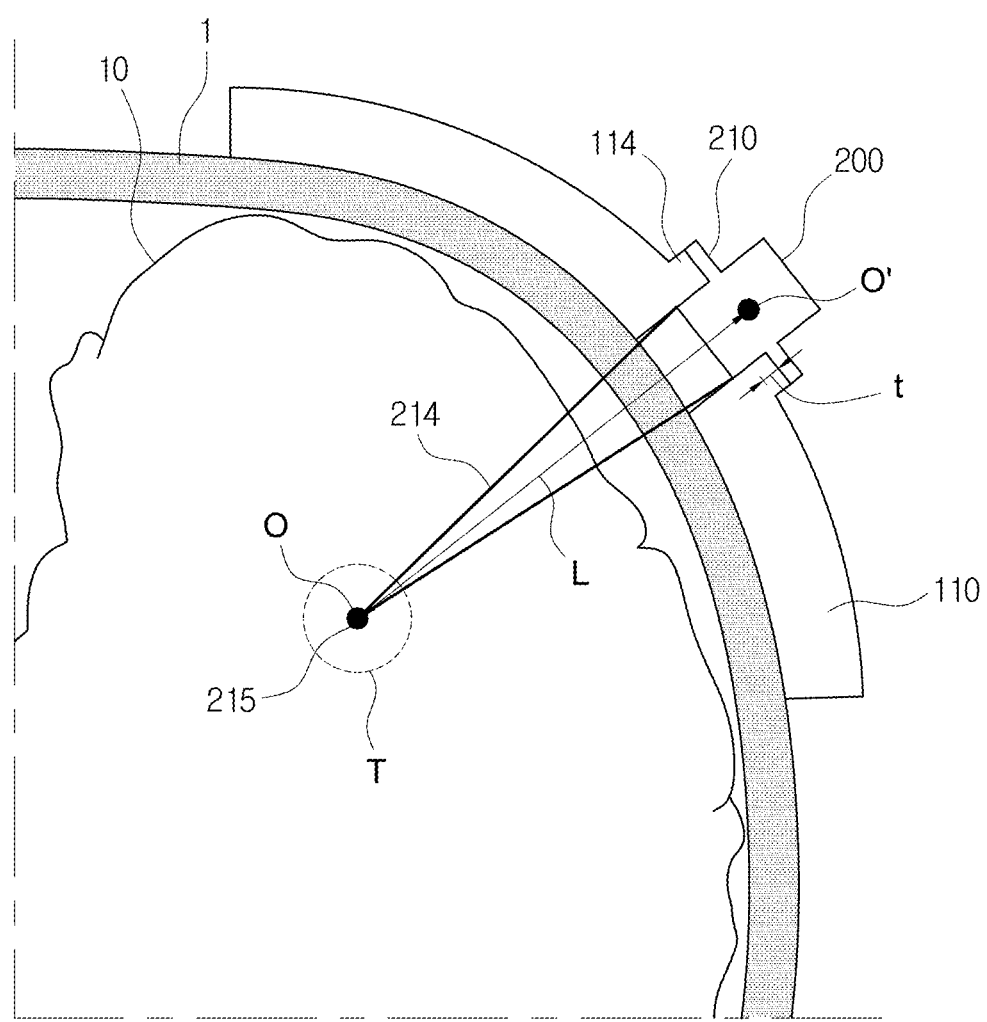
FIG. 8 is a partial schematic diagram showing the ultrasonic stimulation device of FIG. 6 in use.

The ultrasonic transducer 200 generates the focused ultrasound 214 such that the focal point (e.g. target point) 215 is formed at a defined focal length L (see FIG. 8).

Figure 2A:
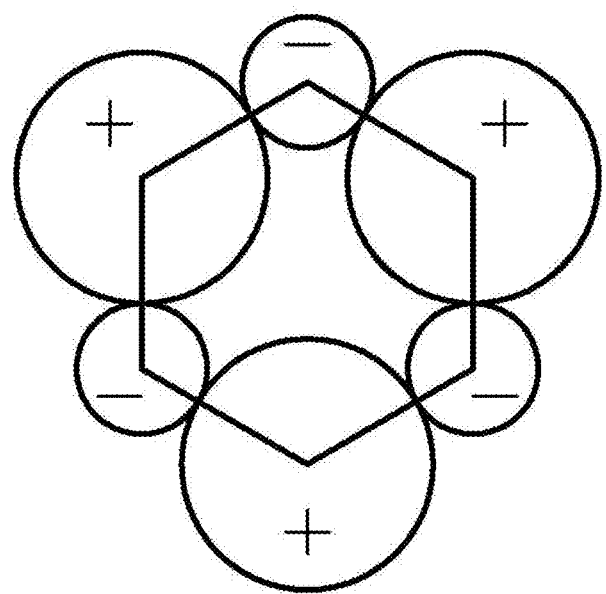
FIGS. 2A to 2C are diagrams illustrating the principle of ultrasound production of an ultrasonic transducer.
Figure 2B:
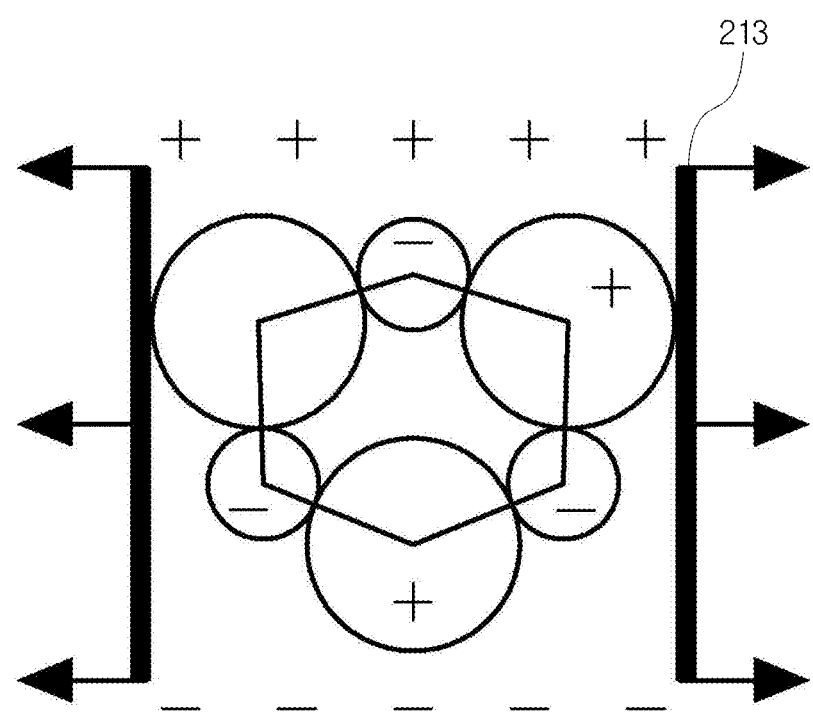
Figure 2C:
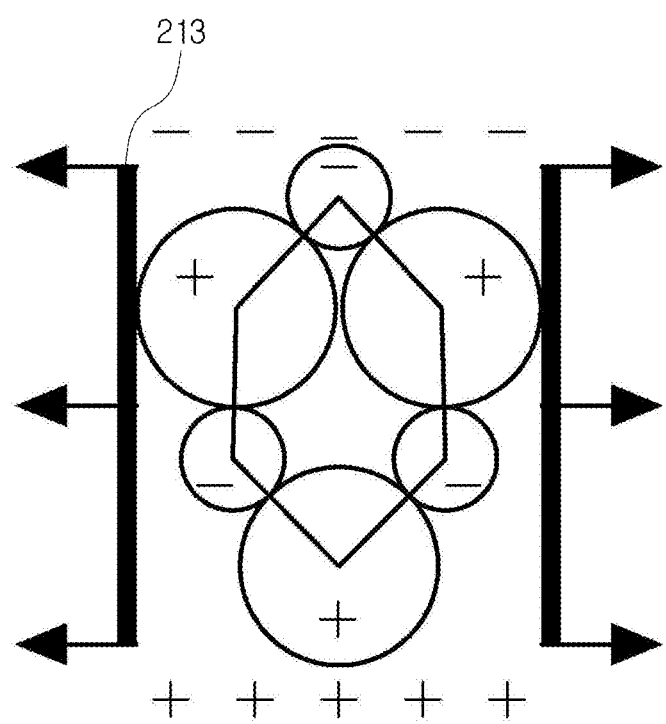
Figure 3:
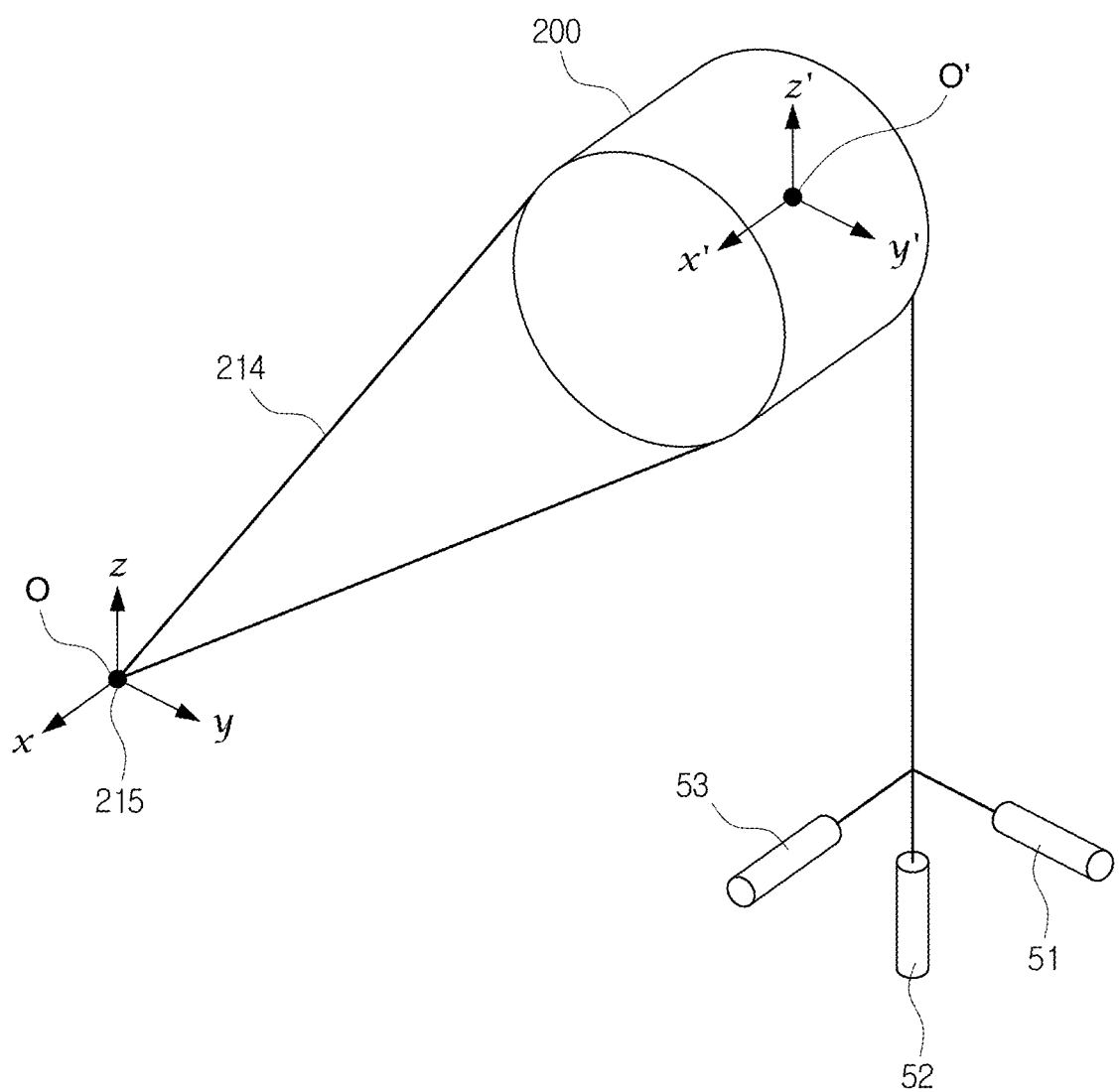
FIG. 3 is a schematic diagram of a positioning tool of an ultrasonic transducer according to the related art.
Figure 4:
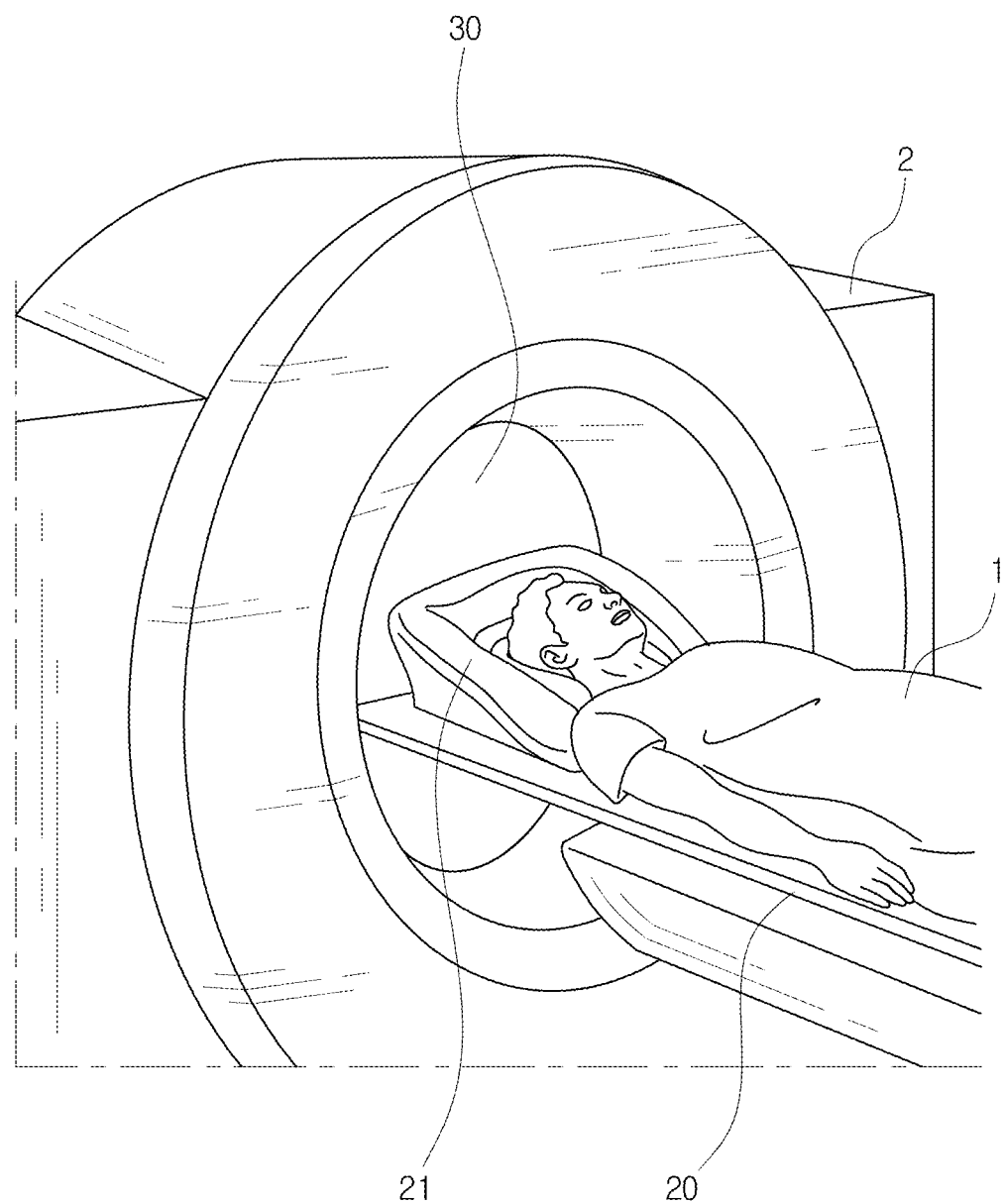
FIGS. 4 and 5 are diagrams illustrating the configuration of a general MRI machine.
Figure 5:
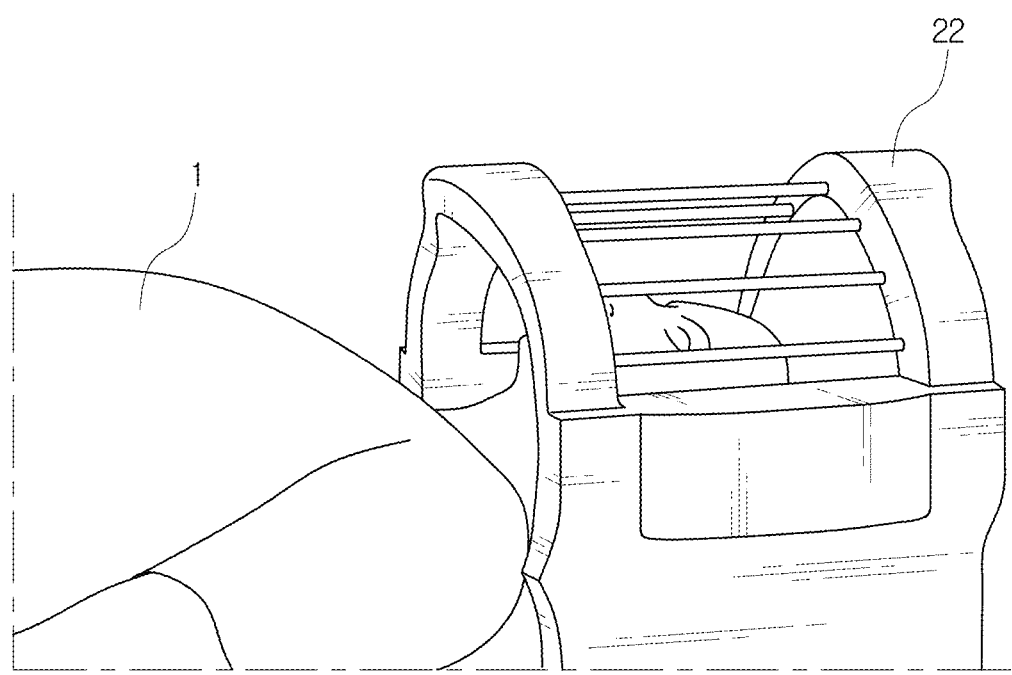

The ultrasonic transducer 200 basically has the same as the structure and operation principle of the ultrasonic transducer as described through FIGS. 1 and 2. In case that the ultrasonic transducer 200 is used in an MRI machine, the ultrasonic transducer 200 may have an MRI-compatible structure with the components made of an MRI-compatible material.

MRI-compatible ultrasonic transducers are commercially available, and a detailed description of their configuration and operation principle is omitted herein.

In case that the ultrasonic transducer 200 is used in an MRI machine, the ultrasonic transducer 200 is connected to a coated electric wire 201 to ensure MRI-compatibility, and the electric wire 201 is connected to the control room of the MRI machine. When the subject 1 is disposed in the MRI machine, the operation of the ultrasonic transducer 200 may be controlled from the control room.

The inner surface 112 of the mask body 110 according to this embodiment has a shape conforming the facial contour of the subject 1 on which the mask body 110 is laid.

In the specification, the shape conforming the facial contour may a shape allowing the inner surface to be placed in close contact with the face by reflecting the entire shape of the facial part covered with the mask body 110, as well as a shape allowing the contour of the face of the subject 1 including nose, cheek and eyes to support the mask body 110.

According to this embodiment, only if the mask body 110 is laid on the face of the subject 1, the inner surface 112 of the mask body 110 is placed at a preset location on the face of the subject 1. Accordingly, only if the positioning hole 120 is formed at an appropriately set location, the ultrasonic transducer 200 can be placed at a desired preset location only by an operation of laying the mask body 110 on the face of the subject 1.

FIG. 8 is a partial schematic diagram showing the guide framework 100 in use.

As shown in FIG. 8, when the ultrasonic transducer 200 is inserted into the positioning hole 120, the position of the focal point 215 of the focused ultrasound 214 produced by the ultrasonic transducer 200 is placed at the preset stimulation location T of the brain 10.

Figure 12A:
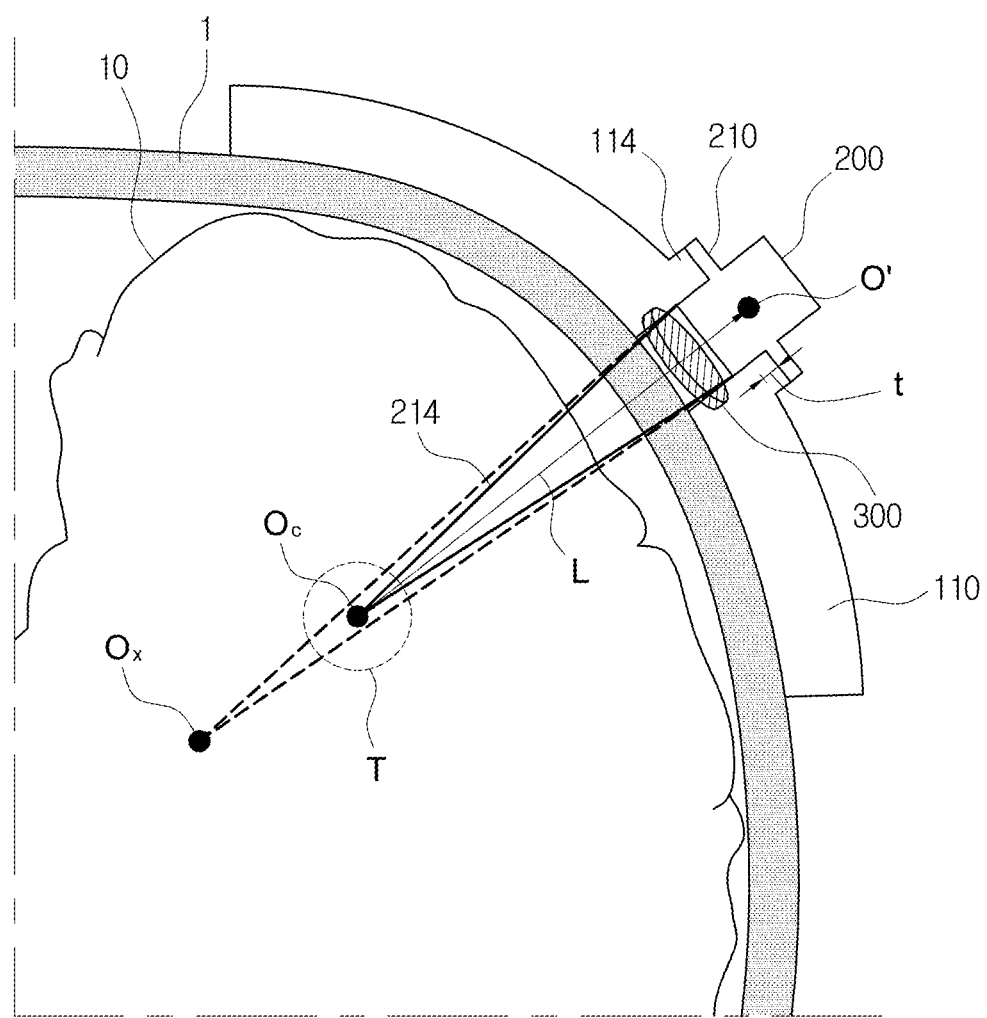
FIGS. 12A and 12B are schematic diagrams showing the ultrasonic stimulation device that can adjust the target point using an acoustic lens.
Figure 12B:
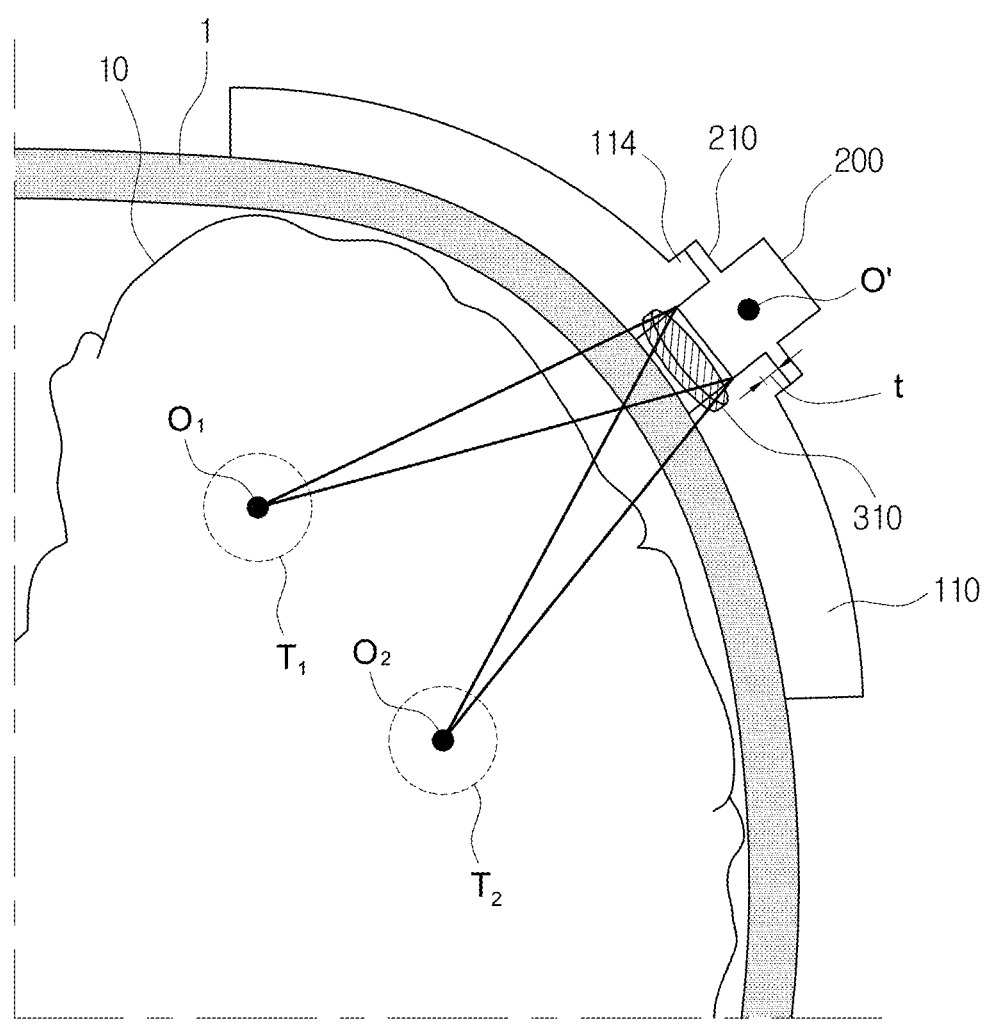

FIGS. 12A and 12B are schematic diagrams showing the ultrasonic stimulation device that can adjust the target point using an acoustic lens.

As shown in FIG. 12A, the guide framework may further include an acoustic lens 300 inserted into the positioning hole 120 to correct the position of the focal point to which the ultrasound is focused.

In reality, although the guide framework is designed to focus ultrasound to a desired focal point, a position mismatch error between a real focal point and an ideal focal point may occur due to an imperfect manufacturing process or acoustic path change through a skull. To solve the problem, the acoustic lens 300 is disposed between the ultrasonic transducer and the face of the subject to correct the focal point.

Referring to FIG. 12A, when the acoustic lens is not inserted, the target position $O_x$ may deviate from the stimulation location T due to an error. In this case, by inserting the acoustic lens 300, it is possible to correct the ultrasonic wave to be focused at the correct target point $O_c$.

The positioning hole of the guide framework may be configured to easily attach and detach the acoustic lens. When ultrasound is not focused to a desired focus position while a user is monitoring MRI images, the user can identify whether ultrasound is focused to an appropriate location while replacing the acoustic lens, in order to correct the position of the focal point to a different direction.

In an embodiment, the acoustic lens may be tailored to focus the ultrasound to at least two target focal points separately.

In the field of ultrasonic stimulation devices, a multifocal ultrasonic stimulation device using multiple ultrasonic transducers is relatively high-priced medical equipment. However, according to this embodiment, by the insertion of the acoustic lens tailored to deliver stimulation to two or more different target focal points, it is possible to stimulate two or more target sites simultaneously using a relatively low-priced single ultrasonic transducer.

In another embodiment, as shown in FIG. 12B, it is possible to stimulate different target positions $O_1$ and $O_2$ simultaneously, by inserting a customized acoustic lens 310 to stimulate different stimulation locations T1 and T2.

The acoustic lens may be formed by a 3-dimensional (3D) printing process.

The ultrasonic transducer 200 according to this embodiment has a flange 210 in the shape of a ring around the body 211. When the ultrasonic transducer 200 is inserted into the positioning hole 120 such that the flange 210 is placed in close contact with the outer surface of the mask body 110 around the positioning hole 120, the ultrasonic transducer 200 is located right in the positioning hole 120.

In an embodiment, the ultrasonic transducer 200 may be a single-element transducer which focus ultrasound in one fixed target point, or a multi-array transducer which can reposition the target point by controlling elements within the transducer. In the case of using the multi-array transducer, the target point can be adjusted even after inserting the transducer into the positioning hole 120 of the guide framework.

In this embodiment, the radius of the positioning hole 120 is substantially the same as the radius of the ultrasonic transducer 200, so that the ultrasonic transducer 200 can be inserted into the positioning hole 120 without applying great force. However, the inner surface of the positioning hole 120 and the outer surface of the body of the ultrasonic transducer 200 may have threads to screw-couple the two members.

The thickness of the mask body 110 may be limited in consideration of the weight burden the subject 1 feels or the size, and the thickness of the mask body 110 may be smaller or larger to meet the depth of focus. Accordingly, as shown in FIG. 8, a protrusion 114 or recess with a height t may be formed around the circumference of the positioning hole 120.

The flange 210 is support on the protrusion 114, and there may be an effect of the movement of the focus position of the ultrasonic transducer 200 close to the skull by the height t by virtue of the protrusion 114. On the contrary, in case that a ring-shaped recess with the height t into which the flange 210 can be inserted is formed, there is an effect on the movement of the focus position of the ultrasonic transducer 200 inward the skull by the height t by virtue of the protrusion 114.

The guide framework 100 according to this embodiment is formed by a 3D printing process. In the embodiment, a method for manufacturing the guide framework may include the following process.

First, contour information is collected by scanning the facial contour of the subject 1. Subsequently, 3D coordinates of the stimulation location T are set, and center coordinates O' of the ultrasonic transducer 200 are set in consideration of the focal length L so that the focal point is placed at the corresponding stimulation location T.

The central position of the positioning hole 120 and the height of the protrusion 114 are set using the shape information of the ultrasonic transducer 200 to position the ultrasonic transducer 200 at the center coordinates O'. Finally, a desired thickness and size of the mask body 110 is set.

The facial contour information, the center coordinates, the central position, the height of the protrusion, and the thickness and size information of the mask body are inputted into a 3D printer (for example, images including the information may be stored after being converted to STL format that can be recognized by the 3D printer), and forming of the guide framework 100 is carried out through the 3D printer.

When the ultrasonic transducer 200 is inserted into the positioning hole 120 of the guide framework 100, and then, the guide framework 100 is laid on the face the subject 1 (the guide framework 100 may be put and then the ultrasonic transducer may be inserted), the position of the focal point of the ultrasonic transducer 200 will be naturally placed at a preset stimulation site T of the brain.

According to an embodiment, a computer program for realizing the process for manufacturing the guide framework may be provided as software.

According to this embodiment, in case of multiple sites to stimulate, multiple guide frameworks may be formed in consideration of multiple focus positions, and one guide framework may be replaced with another guide framework immediately after a stimulation surgery for one stimulation site is completed, and then ultrasonic stimulation may be performed on another stimulation site determined by the corresponding guide framework.

In another embodiment, in case of multiple sites to stimulate, the guide framework further including additional positioning holes may be manufactured in which additional ultrasonic transducers for focusing the ultrasound to focal points different from the focal point are inserted into the additional positioning holes.

Furthermore, in case that an acoustic lens is used as described previously, the focal point can be changed only by additionally inserting the acoustic lens tailored for different focal points into the positioning hole without replacing the guide framework, so that another location can be stimulated easily and quickly.

According to this embodiment, the guide framework 100 can be formed in a very short time at a low cost through a 3D printing process, and thus, the guide framework can be replaced in a simple manner.

One guide framework guarantees that the determined stimulation location matches the focus position of the ultrasonic transducer 200, and thus, only if the guide framework is replaced, there is no need to control the position of the ultrasonic transducer 200 by many calculations. Accordingly, it is possible to determine the focus position with no use of motors.

Meanwhile, although the ultrasonic stimulation device includes the guide framework and the ultrasonic transducer in the above embodiment, the ultrasonic stimulation device may further include a fixing device to fix the ultrasonic transducer in consideration of a rise in supporting force of the ultrasonic transducer.

Figure 9:
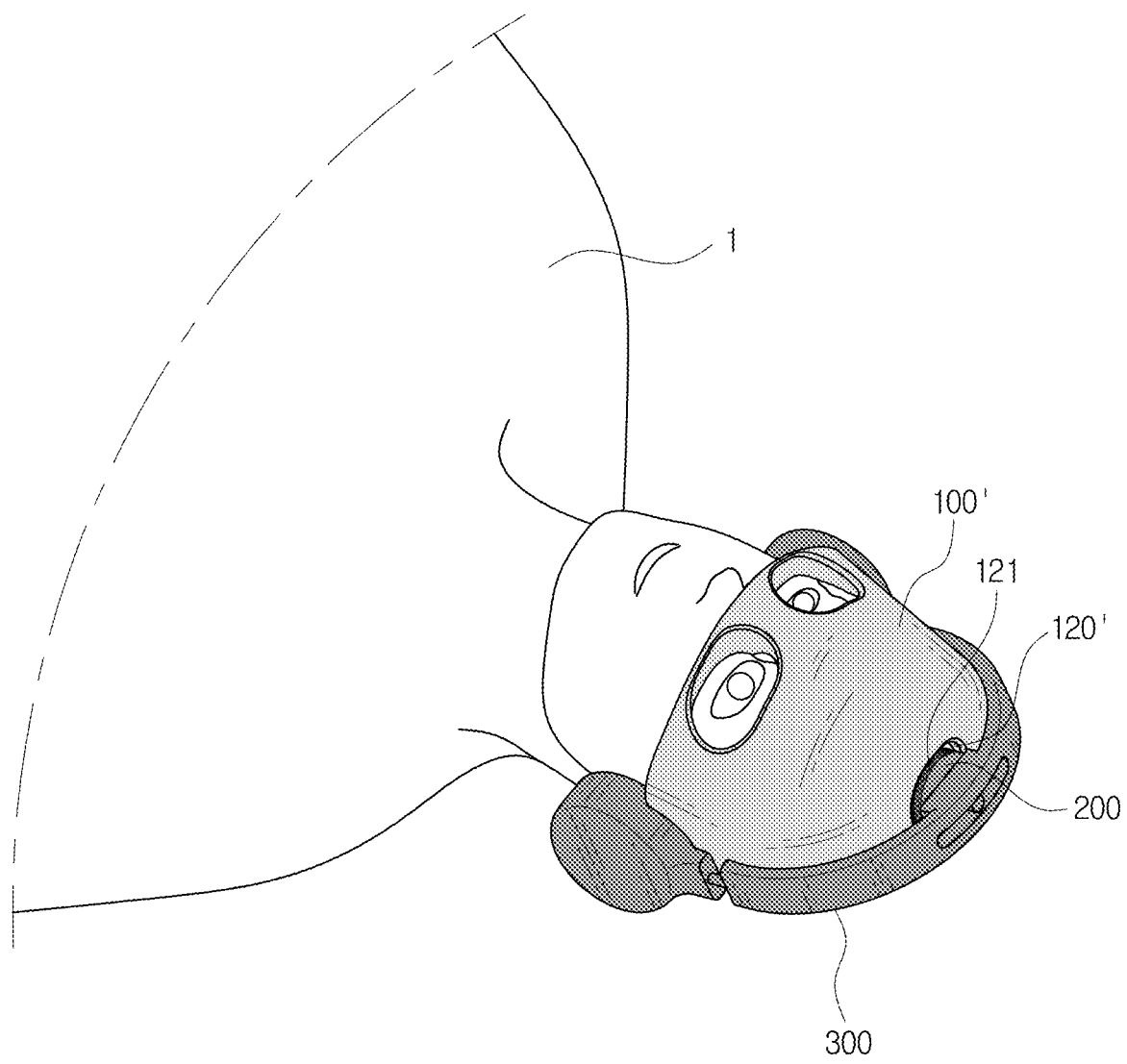
FIG. 9 shows an ultrasonic stimulation device according to another embodiment of the present disclosure.

FIG. 9 shows an ultrasonic stimulation device according to another embodiment of the present disclosure.

The ultrasonic stimulation device includes a headphone-type fixing device 300 that is supported on the side of the face of the subject 1, covering the ears.

Figure 10:
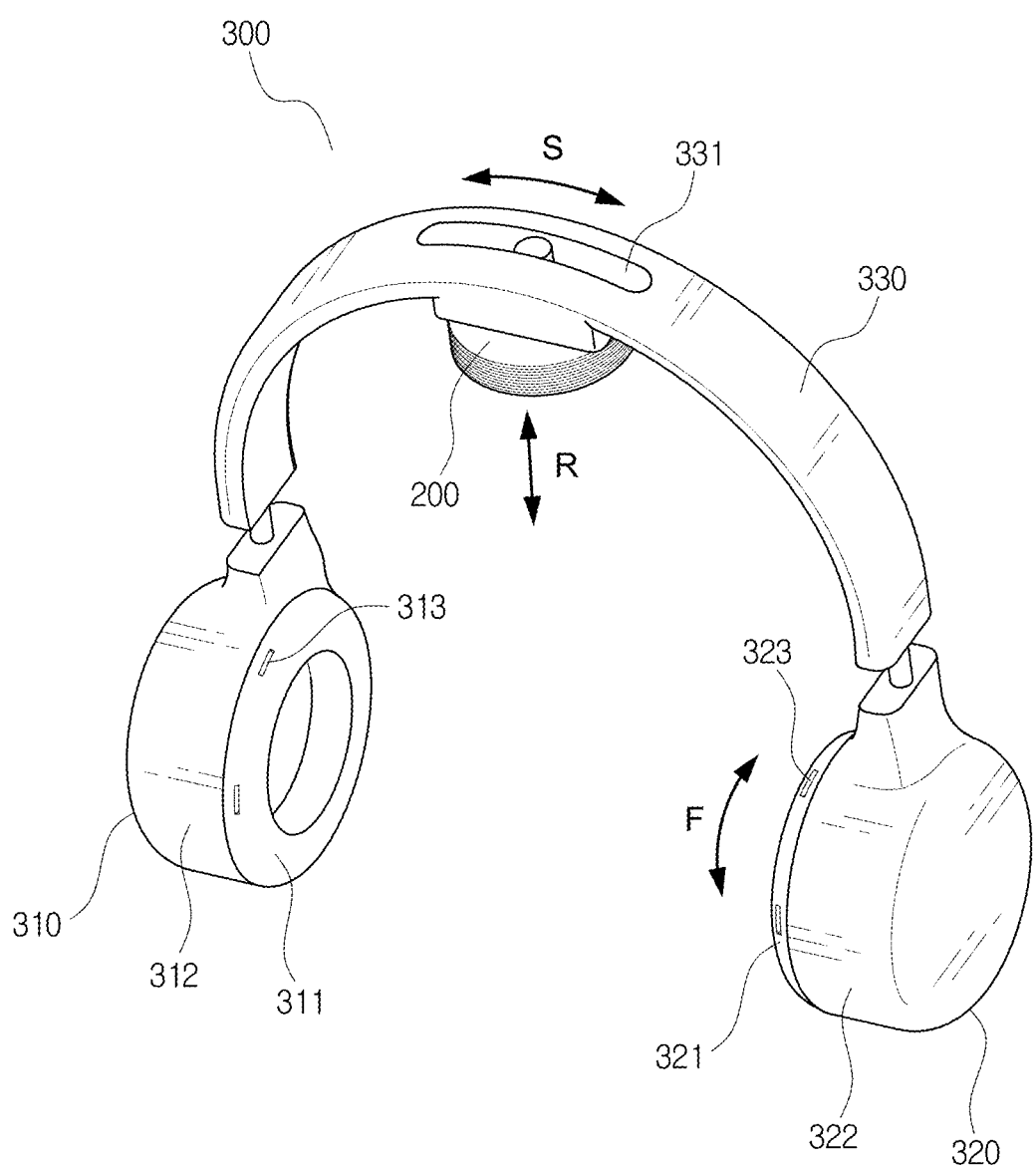
FIG. 10 is a perspective view of a fixing device of the ultrasonic stimulation device of FIG. 9.

FIG. 10 is a perspective view of the fixing device 300.

Referring to FIG. 10, the fixing device 300 includes two earmuffs 310, 320 that cover two ears of the subject 1, and an arch-shaped connecting member 330 connecting the two earmuffs 310, 320. The ultrasonic transducer 200 is connected to the inside of the radius of the connecting member 330.

One earmuff 310 includes a fixing part 311 that is placed in close contact with the ear of the subject 1 and a rotating part 312 that can rotate with respect to the fixing part 311. The other earmuff 320 also includes a fixing part 321 and a rotating part 322.

As the rotating parts rotate with respect to the fixing parts of the earmuffs, the connecting member 330 rotates in F direction, and the ultrasonic transducer 200 connected to the connecting member 330 rotates in F direction. By the rotation in F direction, the position of the ultrasonic transducer 200 can be moved in the anterior-posterior direction of the head of the subject 1.

The connecting member 330 has a slit 331 along the lengthwise direction, and a pin member that fixes the ultrasonic transducer 200 can slide along the slit 331. Accordingly, the ultrasonic transducer 200 can move the position in the lengthwise direction (lateral direction) S of the connecting member 330.

Furthermore, the ultrasonic transducer 200 is screw-coupled with the pin member and the ultrasonic transducer 200 can move the position in the radial direction R of the connecting member 330 apart from or close to the connecting member 330.

Accordingly, the position of the ultrasonic transducer 200 can be adjusted in 3D with respect to the subject 1 by the fixing device 300.

Figure 11:
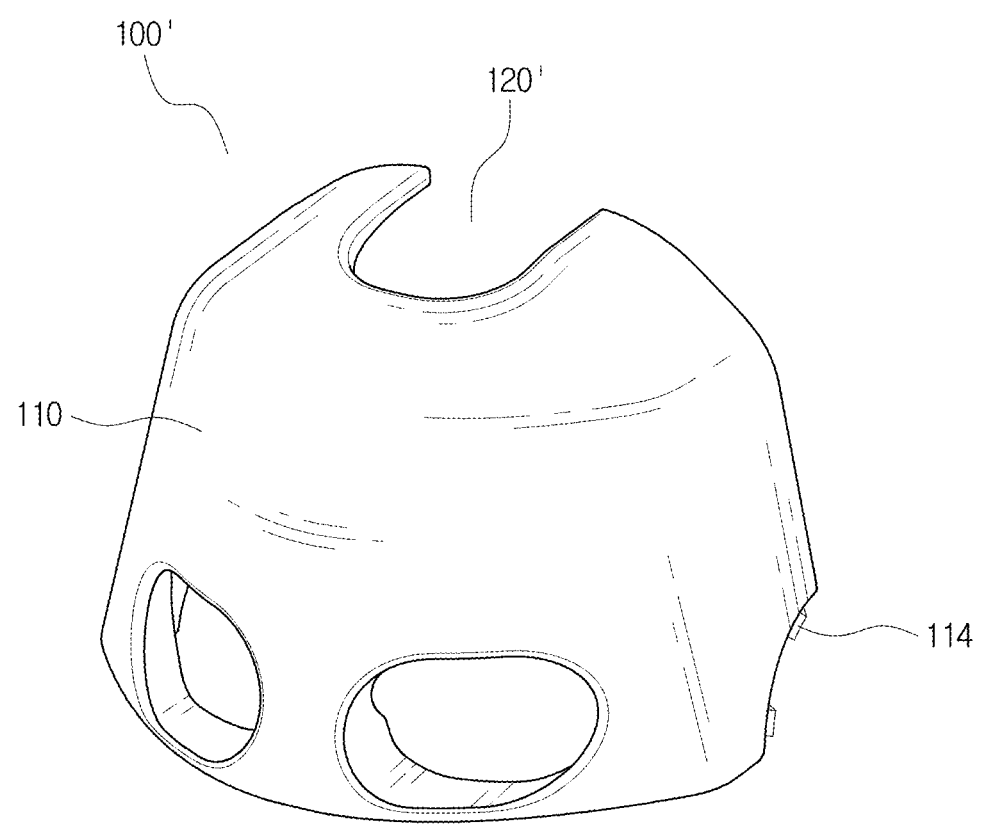
FIG. 11 is a perspective view of a guide framework of the ultrasonic stimulation device of FIG. 9.

FIG. 11 is a front perspective view of a guide framework 100' according to this embodiment.

As shown in FIG. 11, a positioning hole 120' of the guide framework 100' is formed of a slit that is cut open to the back of the mask body 110.

Referring back to FIG. 9, when the ultrasonic transducer 200 is placed in close contact with an edge 121 on the opposite side of the opening of the slit of the positioning hole 120', the position of the focal point of the focused ultrasound is naturally placed at the preset stimulation site of the brain.

The inner surface of the guide framework 100' according to this embodiment is formed with a shape that matches the facial contour of the subject.

The guide framework 100' and the fixing device 300 according to this embodiment are formed such that they can be connected and fixed to each other.

Referring back to FIGS. 10 and 11, engagement protrusions 114 are formed on the side of the guide framework 100' adjacent to the earmuffs of the fixing device 300. In match with this, the fixing parts 311, 321 of the earmuffs of the fixing device 300 have engagement grooves 313, 323 into which the engagement protrusions 114 are inserted.

When the engagement protrusions of the guide framework 100' formed to make a specific focus position are inserted into the engagement grooves of the fixing device 300, and then, the guide framework 100' is laid on the face of the subject 1, a position fixing hole 120' is naturally positioned right at a desired location, and at the same time, the earmuffs 310, 320 of the fixing device 300 are placed wrapping around the ears of the subject.

Subsequently, when the position of the ultrasonic transducer 200 is adjusted by adjusting the fixing device 300 so that the ultrasonic transducer 200 is placed in close contact with the edge of the slit of the position fixing hole 120', the ultrasonic transducer 200 is naturally positioned at a correct position so that the focus position of the ultrasonic transducer 200 is placed at the stimulation location. Although not shown in detail, the fixing device 300 may include a locking device to fix the position of the ultrasonic transducer 200.

According to this structure, the ultrasonic transducer 200 is naturally positioned by the guide framework 100', and the position of the ultrasonic transducer 200 can be fixed more stably by the guide framework 100' and the fixing device 300.

However, in the absence of the engagement protrusions and the engagement grooves, the guide framework 100' and the fixing device 300 are not fixed and may be independently formed, and in this case, the ultrasonic transducer 200 can be also positioned only by the shape of the guide framework 100' without any problem.

In case that the guide framework 100' and the fixing device 300 are independently formed, the position fixing hole 120' is open to one side, and thus, after the ultrasonic transducer 200 is placed at a correct location and the position is fixed by the fixing device 300, the guide framework 100' may be removed from the face. When the guide framework 100' is removed, an uneasy or trapped feeling of the subject during stimulation surgery will be mitigated.

According to an embodiment, the earmuffs of the fixing device 300 may be formed with a real headphone structure of an MRI-compatible structure. Accordingly, intentions such as various types of directions or instructions from the control room can be transmitted to the subject 1 in the MRI machine as a voice.

According to the ultrasonic stimulation device of the embodiments, it is possible to place the focus position at a desired location in the absence of large and complex elements such as motors for determining and controlling the position of the ultrasonic transducer, thus allowing applications in the narrow internal space of the MRI machine.

The guide framework can be produced quickly in a large amount at a low cost through a 3D printing process, significantly reducing the efforts and time for calibrating and controlling the focus position.

The ultrasonic stimulation device has an MRI-compatible structure, and thus can operate in an MRI environment, and stimulation condition can be monitored in real time through imaging of the MRI machine while ultrasonic stimulation is being performed.

What is claimed is:

1. An ultrasonic stimulation device for carrying out surgery to apply an ultrasonic stimulation to a subject's brain, the ultrasonic stimulation device comprising:
   an ultrasonic transducer configured to emit a focused ultrasound to a target point; and
   a guide framework for positioning the ultrasonic transducer,
   wherein the guide framework comprises:
   a body in a shape of a mask that is configured to be lain on the subject's face;
   a positioning hole formed through an inner surface and an outer surface of the body, the positioning hole into which the ultrasonic transducer is inserted; and
   a fixing device, which has a shape of a headphone that is supported and fixed on a side of the subject's face, for fixing the ultrasonic transducer and adjusting a position of the ultrasonic transducer in 3 dimensions to dispose the ultrasonic transducer at the positioning hole,
   wherein the inner surface of the body is formed to conform to a facial contour of the subject,
   wherein with the guide framework lain on the subject's face and the ultrasonic transducer disposed at the positioning hole, a position of the target point is naturally disposed at a preset stimulation site of the brain,
   wherein the guide framework is formed using a 3-dimensional printer based on the facial contour of the subject and the preset stimulation site of the brain,
   wherein the body of the guide framework is formed to cover an upper part of the subject's face with the subject's nose uncovered,
   wherein the body of the guide framework is formed to have openings so as not to cover the subject's eyes,
   wherein the fixing device comprises:
   two earmuffs which cover two ears of the subject; and an arch-shaped connecting member connecting the two earmuffs, wherein the ultrasonic transducer is connected to the arch-shaped connecting member, wherein the arch-shaped connecting member is rotatable frontward and rearward of the subject with respect to the earmuffs, wherein the ultrasonic transducer is moveable laterally along a lengthwise direction of the arch-shaped connecting member, and wherein the ultrasonic transducer is moveable in a radius direction apart from or close to the arch-shaped connecting member, wherein the guide framework is manufactured using the 3-dimensional printer by:

collecting contour information by scanning the subject's facial contour, setting 3D coordinates of the stimulation site, setting a center coordinate of the ultrasonic transducer to allow a focal point of the ultrasonic transducer to be located at the stimulation site in consideration of a focal length of the ultrasonic transducer, using shape information of the ultrasonic transducer, setting a center position of the positioning hole and a height of a protrusion provided on the body of the guide framework to allow the ultrasonic transducer to be located at the center coordinate, and setting a desired thickness and a desired size of the mask body.

2. The ultrasonic stimulation device according to claim 1, wherein the positioning hole is formed of a slit that is cut open to one side of the body, and wherein with the ultrasonic transducer disposed at an edge on an opposite side of an opening of the slit, the position of the target point is naturally disposed at the preset stimulation site of the brain.

3. The ultrasonic stimulation device according to claim 1, wherein the positioning hole is formed in a shape of a slit that is cut open to one side of the body, and wherein with the ultrasonic transducer fixedly positioned at an edge on an opposite side of an opening of the slit, the guide framework is removable.

4. The ultrasonic stimulation device according to claim 1, wherein the guide framework further comprises an acoustic lens which is inserted into the positioning hole and disposed between the ultrasonic transducer and the subject's face to correct the position of the target point to which an ultrasound is focused.

5. The ultrasonic stimulation device according to claim 4, wherein the acoustic lens is tailored to focus the ultrasound to at least two target points separately.

6. The ultrasonic stimulation device according to claim 4, wherein the acoustic lens is formed by a 3-dimensional printing process.

7. The ultrasonic stimulation device according to claim 1, wherein the guide framework further comprises additional positioning holes into which additional ultrasonic transducers for focusing the ultrasound to different target points from the target point are inserted.

8. The ultrasonic stimulation device according to claim 1, wherein the ultrasonic transducer is a multi-array transducer which can reposition the target point by controlling elements within the transducer.

9. The ultrasonic stimulation device according to claim 1, wherein the ultrasonic transducer has a magnetic resonance imaging (MRI) compatible structure, and wherein the ultrasonic transducer is configured to be connected to a control room of an MRI machine by a coated electric wire.

10. The ultrasonic stimulation device according to claim 1, wherein the ultrasonic transducer has a flange in a shape of a ring that is located in close contact with the outer surface of the body around the positioning hole.

11. The ultrasonic stimulation device according to claim 1, wherein the body of the guide framework has a recess formed around a circumference of the positioning hole.

12. The ultrasonic stimulation device according to claim 1, wherein the fixing device includes a headphone structure configured to transmit instructions from a control room to the subject when the ultrasonic stimulation device is used by the subject in an MRI machine.

13. An ultrasonic stimulation device for carrying out surgery to apply an ultrasonic stimulation to a subject's brain, the ultrasonic stimulation device comprising:

an ultrasonic transducer configured to emit a focused ultrasound to a target point; and a guide framework for positioning the ultrasonic transducer, wherein the guide framework comprises:

a body in a shape of a mask that is configured to be lain on the subject's face;

a positioning hole formed through an inner surface and an outer surface of the body, the positioning hole into which the ultrasonic transducer is inserted; and a fixing device, which has a shape of a headphone that is supported and fixed on a side of the subject's face, for fixing the ultrasonic transducer and adjusting a position of the ultrasonic transducer in 3 dimensions to dispose the ultrasonic transducer at the positioning hole, wherein the inner surface of the body is formed to conform to a facial contour of the subject, wherein with the guide framework lain on the subject's face and the ultrasonic transducer disposed at the positioning hole, a position of the target point is naturally disposed at a preset stimulation site of the brain, wherein the guide framework is formed through a 3-dimensional printer based on the facial contour of the subject and the preset stimulation site of the brain, wherein the body of the guide framework is formed to cover an upper part of the subject's face with the subject's nose uncovered, wherein the body of the guide framework is formed to have openings so as not to cover the subject's eyes, wherein the fixing device comprises:

two earmuffs which cover two ears of the subject; and an arch-shaped connecting member connecting the two earmuffs, wherein the ultrasonic transducer is connected to the arch-shaped connecting member, wherein the arch-shaped connecting member is rotatable frontward and rearward of the subject with respect to the earmuffs, wherein the ultrasonic transducer is moveable laterally along a lengthwise direction of the arch-shaped connecting member, and wherein the ultrasonic transducer is moveable between the arch-shaped connecting member and skin of the subject's skull in a direction away from or toward the skin of the skull.

14. The ultrasonic stimulation device according to claim 13, wherein the positioning hole is formed of a slit that is cut open to one side of the body, and wherein with the ultrasonic transducer disposed at an edge on an opposite side of an opening of the slit, the position of the target point is naturally disposed at the preset stimulation site of the brain.

15. The ultrasonic stimulation device according to claim 13, wherein the positioning hole is formed in a shape of a slit that is cut open to one side of the body, and wherein with the ultrasonic transducer fixedly positioned at an edge on an opposite side of an opening of the slit, the guide framework is removable.

16. The ultrasonic stimulation device according to claim 13, wherein the guide framework further comprises an acoustic lens which is inserted into the positioning hole and disposed between the ultrasonic transducer and the subject's face to correct the position of the target point to which an ultrasound is focused.

17. The ultrasonic stimulation device according to claim 16, wherein the acoustic lens is tailored to focus the ultrasound to at least two target points separately.

* * * * *